US012788555B2

(12) United States Patent
Hendrickson et al.

(10) Patent No.: US 12,788,555 B2
(45) Date of Patent: Nov. 10, 2026

(54) HYDRAULIC DELIVERY OF SURGICAL IMPLANTS

(71) Applicant: Alcon Inc., Fribourg (CH)

(72) Inventors: Kathryn Hendrickson, Sugar Land, TX (US); Jestwin Edwin Lee, IV, Grandview, TX (US); Todd Taber, Keller, TX (US); Stephen John Collins, San Francisco, CA (US); Ryan Michael Miller, Grand Prairie, TX (US); Thaddeus Scott Milburn, Pantego, TX (US)

( * ) Notice: Subject to any disclaimer, the term of this patent is extended or adjusted under 35 U.S.C. 154(b) by 183 days.

(21) Appl. No.: 18/931,296

(22) Filed: Oct. 30, 2024

(65) Prior Publication Data

US 2025/0134650 A1 May 1, 2025

Related U.S. Application Data

(60) Provisional application No. 63/594,856, filed on Oct. 31, 2023.

(51) Int. Cl.
*A61F 2/16* (2006.01)

(52) U.S. Cl.
CPC .................................... *A61F 2/167* (2013.01)

(58) Field of Classification Search
CPC ...... A61F 2/1662; A61F 2/167; A61F 2/1675; A61F 2250/0007; A61F 2250/0065
See application file for complete search history.

(56) References Cited

U.S. PATENT DOCUMENTS

| | | | |
|---|---|---|---|
| 5,873,879 | A | 2/1999 | Figueroa et al. |
| 7,156,854 | B2 | 1/2007 | Brown et al. |
| 8,105,332 | B2 | 1/2012 | Downer et al. |
| 8,308,736 | B2 | 11/2012 | Boukhny et al. |
| 8,308,799 | B2 | 11/2012 | Chen et al. |
| 8,377,076 | B2 | 2/2013 | Downer et al. |
| 8,801,780 | B2 | 8/2014 | Chen |
| 8,956,408 | B2 | 2/2015 | Smiley et al. |
| 8,968,396 | B2 | 3/2015 | Matthews et al. |
| 9,480,555 | B2 | 11/2016 | Downer et al. |
| 9,610,155 | B2 | 4/2017 | Matthews et al. |

(Continued)

FOREIGN PATENT DOCUMENTS

| | | |
|---|---|---|
| DE | 102019115125 | 9/2020 |
| EP | 1800623 A1 | 6/2007 |

(Continued)

OTHER PUBLICATIONS

U.S. Appl. No. 63/263,948, filed Nov. 12, 2021, Harlen Hoang (Continued)

*Primary Examiner* — Ryan J. Severson
(74) *Attorney, Agent, or Firm* — Cherry Johnson Siegmund James PC; Darin Deaver

(57) ABSTRACT

An apparatus for delivering an implant to an eye using a push rod and hydraulic fluid flow or pressure. An implant may be stored, advanced, and delivered to an eye using hydraulic fluid, which can be stored in the apparatus or a sterile container and delivered through the push rod. The plunger may rigidly advance the implant to a sealed position in a first phase, and then the implant may be advanced into the eye via hydraulic pressure or fluid flow in a second phase.

21 Claims, 12 Drawing Sheets

(56) References Cited

U.S. PATENT DOCUMENTS

| | | | | |
|---|---|---|---|---|
| 9,693,858 | B2 | 7/2017 | Hildebrand et al. | |
| 9,855,139 | B2 | 1/2018 | Matthews et al. | |
| 10,172,706 | B2 | 1/2019 | Auld et al. | |
| 10,195,020 | B2 | 2/2019 | Matthews et al. | |
| 10,397,104 | B2 * | 8/2019 | Johnsen | H04L 45/04 |
| 10,568,735 | B2 | 2/2020 | Brown et al. | |
| 10,588,780 | B2 | 3/2020 | Van Noy et al. | |
| 11,039,953 | B2 | 6/2021 | Balachandran | |
| 11,839,537 | B2 * | 12/2023 | Taber | A61F 2/167 |
| 11,925,548 | B2 * | 3/2024 | Taber | A61F 2/167 |
| 12,004,944 | B2 | 6/2024 | Weston | |
| 12,156,805 | B2 | 12/2024 | Taber et al. | |
| 12,251,306 | B2 * | 3/2025 | Taber | A61F 2/167 |
| 2008/0097460 | A1 | 4/2008 | Boukhny et al. | |
| 2008/0147081 | A1 | 6/2008 | Pynson | |
| 2008/0221584 | A1 | 9/2008 | Downer | |
| 2009/0318933 | A1 | 12/2009 | Anderson | |
| 2010/0057093 | A1 | 3/2010 | Ide et al. | |
| 2010/0125278 | A1 | 5/2010 | Wagner | |
| 2011/0265779 | A1 | 11/2011 | Vandrak et al. | |
| 2012/0022548 | A1 | 1/2012 | Zacharias | |
| 2013/0197532 | A1 | 8/2013 | Boukhny et al. | |
| 2013/0253527 | A1 | 9/2013 | Schneider et al. | |
| 2014/0012277 | A1 | 1/2014 | Matthews et al. | |
| 2014/0257315 | A1 | 9/2014 | Wu | |
| 2014/0276898 | A1 | 9/2014 | Novak et al. | |
| 2015/0238687 | A1 | 8/2015 | Novakovic et al. | |
| 2015/0282928 | A1 | 10/2015 | Auld et al. | |
| 2016/0087460 | A1 | 3/2016 | Rich et al. | |
| 2017/0007237 | A1 | 1/2017 | Yates et al. | |
| 2017/0027686 | A1 | 2/2017 | Nagasaka et al. | |
| 2017/0119522 | A1 | 5/2017 | Auld et al. | |
| 2017/0135811 | A1 | 5/2017 | Springer et al. | |
| 2017/0257315 | A1 * | 9/2017 | Johnsen | H04L 45/04 |
| 2018/0049866 | A1 | 2/2018 | Fayyaz et al. | |
| 2018/0200046 | A1 | 7/2018 | Brown et al. | |
| 2018/0200047 | A1 | 7/2018 | Wu et al. | |
| 2019/0224002 | A1 | 7/2019 | Springer et al. | |
| 2020/0015959 | A1 | 1/2020 | Wensrich et al. | |
| 2020/0038171 | A1 | 2/2020 | Glick et al. | |
| 2020/0179101 | A1 | 6/2020 | Flowers et al. | |
| 2020/0179102 | A1 | 6/2020 | Chen et al. | |
| 2020/0179103 | A1 | 6/2020 | Auld et al. | |
| 2020/0188089 | A1 | 6/2020 | Auld et al. | |
| 2020/0197168 | A1 | 6/2020 | Wu et al. | |
| 2020/0197170 | A1 | 6/2020 | Auld et al. | |
| 2021/0038369 | A1 | 2/2021 | Holderby | |
| 2021/0052371 | A1 | 2/2021 | Singh et al. | |
| 2021/0369446 | A1 | 12/2021 | Taber et al. | |
| 2022/0142767 | A1 | 5/2022 | Taber et al. | |
| 2022/0175517 | A1 | 6/2022 | Lee, IV et al. | |
| 2022/0192819 | A1 | 6/2022 | Rodeheaver et al. | |
| 2022/0265420 | A1 | 8/2022 | Kelp | |
| 2023/0097833 | A1 | 3/2023 | Wu | |
| 2023/0131381 | A1 | 4/2023 | Hoang | |
| 2023/0149155 | A1 | 5/2023 | Hoang et al. | |
| 2023/0277302 | A1 | 9/2023 | Wu et al. | |
| 2023/0301833 | A1 * | 9/2023 | Wu | A61F 2/1672 |
| 2024/0016600 | A1 * | 1/2024 | Taber | A61F 2/167 |
| 2024/0090997 | A1 * | 3/2024 | Taber | A61F 2/167 |
| 2025/0041050 | A1 * | 2/2025 | Taber | A61F 2/167 |
| 2025/0134650 | A1 * | 5/2025 | Hendrickson | A61F 2/167 |
| 2025/0177123 | A1 * | 6/2025 | Taber | A61F 2/167 |

FOREIGN PATENT DOCUMENTS

| | | | |
|---|---|---|---|
| EP | 1857076 | B1 | 7/2010 |
| EP | 2873391 | A1 | 5/2015 |
| EP | 3560457 | A1 | 10/2019 |
| JP | 2007244570 | A | 9/2007 |
| JP | 2010063777 | B | 10/2013 |
| JP | 2016503716 | A | 2/2016 |
| WO | 9637152 | A1 | 11/1996 |
| WO | 2006059183 | A1 | 6/2006 |
| WO | 2014145562 | A1 | 9/2014 |
| WO | 2016141308 | A1 | 9/2016 |
| WO | 2020065516 | A1 | 4/2020 |
| WO | 2020128762 | A1 | 6/2020 |
| WO | 2020151908 | A1 | 7/2020 |
| WO | 2021154203 | A1 | 8/2021 |
| WO | 2022101690 | A1 | 5/2022 |
| WO | 2022118249 | A1 | 6/2022 |

OTHER PUBLICATIONS

U.S. Appl. No. 63/268,704, filed Mar. 1, 2022, Yinghui Wu.

Feb. 6, 2023 International Search Report and Written Opinion of the International Searching Authority PCT/IB2022/060155.

Written Opinion of the International Searching Authority PCT/IB2023/057106 (Oct. 24, 2023).

* cited by examiner

HYDRAULIC DELIVERY OF SURGICAL IMPLANTS

PRIORITY CLAIM

This application claims the benefit of priority of U.S. Provisional Patent Application Ser. No. 63/594,856 titled “Hydraulic Delivery of Surgical Implants”, filed on Oct. 31, 2023, whose inventor(s) is/are Kathryn Hendrickson, Jestwin Edwin Lee, IV, Todd Taber, Stephen John Collins, Ryan Michael Miller and Thaddeus Scott Milburn, which is hereby incorporated by reference in its entirety as though fully and completely set forth herein.

TECHNICAL FIELD

The invention set forth in the appended claims relates generally to eye surgery. More particularly, but without limitation, the claimed subject matter relates to systems, apparatuses, and methods for inserting an implant into an eye.

BACKGROUND

The human eye can suffer a number of maladies causing mild deterioration to complete loss of vision. While contact lenses and eyeglasses can compensate for some ailments, ophthalmic surgery may be required for others. In some instances, implants may be beneficial or desirable. For example, an intraocular lens may replace a clouded natural lens within an eye to improve vision.

While the benefits of intraocular lenses and other implants are known, improvements to delivery systems, components, and processes continue to improve outcomes and benefit patients.

BRIEF SUMMARY

New and useful systems, apparatuses, and methods for eye surgery are set forth in the appended claims. Illustrative embodiments are also provided to enable a person skilled in the art to make and use the claimed subject matter.

For example, some embodiments may comprise an apparatus for delivering an implant, such as an intraocular lens. Some embodiments of the apparatus may comprise a plunger or other push rod having a hydraulic seal, which can push a working fluid to drive the implant. For example, the plunger may have a rigid shaft for positioning the implant, and the hydraulic seal may comprise a soft tip coupled to the shaft for delivering the implant.

In other examples, some embodiments may comprise an apparatus for delivering an implant using hydraulic pressure or fluid flow. The apparatus may be combined with a disposable hydraulic driver, such as a vial of working fluid, to provide a fully disposable system for storing, advancing, and delivering an implant. In more particular examples, the apparatus may comprise a rigid plunger for advancing an implant to a sealed position in a first phase, and a bore through the rigid plunger that allows a working fluid to advance the implant into the eye via hydraulic pressure in a second phase. For example, a hollow rigid plunger can be used to first advance an intraocular lens in a straight-straight configuration to a point that a seal is created about the intraocular lens within a delivery lumen. The lens may then be hydraulically advanced to delivery by passing a working fluid through the hollow bore of the plunger.

In some embodiments, the tip of the plunger may have an implant interface, which can actively guide and maintain proper orientation of an implant. For example, the tip may have a notch for engaging a shoulder of the implant and advancing the lens into a delivery lumen.

Some embodiments of the plunger may bend, stretch, or telescope to increase the length of the plunger. For example, the plunger may comprise a rigid distal end with a flexible sleeve that can stretch and provide a flow path through the plunger for a working fluid. If fully extended and the working fluid exceeds a threshold pressure, the working fluid may deliver an implant. The plunger may be compacted down to reduce linear length.

More generally, a plunger for advancing an implant in an implant delivery system may comprise a shaft having a first end, a second end, and a bore between the first end and the second end; an implant interface proximate to the first end and configured to engage the implant; and a fluid coupling proximate to the second end and configured to fluidly couple a working fluid to the bore. Some embodiments may additionally comprise one or more guide fins disposed between the first end and the fluid coupling. For example, a plurality of guide fins may be disposed radially around the shaft in some embodiments. Additionally, or alternatively, the shaft may be extendable in some embodiments. For example, the shaft may comprise at least two articulated sections. In some embodiments, for example, the articulated sections may be concertinaed or telescoping. In more particular embodiments, the shaft may be configured to be extended by the working fluid.

Some embodiments may additionally comprise one or more of a nozzle, an implant bay, and an actuator. For example, an apparatus for ejecting an implant for eye surgery may comprise a nozzle having a delivery lumen and an implant bay coupled to the nozzle. An actuator may be coupled to the implant bay. The actuator may comprise a housing, and the plunger may be disposed within the housing. The implant interface may be configured to advance the implant from the implant bay to the delivery lumen. The bore may be configured to deliver a working fluid to the delivery lumen to advance the implant through the delivery lumen.

Some embodiments of an apparatus for eye surgery may comprise a nozzle having a delivery lumen, an implant bay coupled to the nozzle, a working fluid disposed in the implant bay, and an implant disposed in the working fluid. An actuator may be coupled to the implant bay. The actuator may comprise a housing and a plunger having a seal disposed within the implant bay. The seal may be configured to advance the working fluid and the implant from the implant bay through the delivery lumen to eject the implant. In more particular embodiments, the plunger may comprise a shaft having a first end and a second end, wherein the seal is coupled to the first end. At least one guide fin may be disposed between the first end and the second end within the housing. For example, a plurality of guide fins may be disposed radially around the shaft between the first end and the second end. In some embodiments, the shaft may be extendable. For example, the shaft may comprise at least to articulated sections. Additionally, the shaft may be configured to be extended by a working fluid pushed through a fluid coupling proximate to the second end of the shaft.

Features, elements, and aspects described in the context of some embodiments may also be omitted, combined, or replaced by alternative features. Other features, objectives, advantages, and a preferred mode of making and using the claimed subject matter are described in greater detail below with reference to the accompanying drawings of illustrative embodiments.

BRIEF DESCRIPTION OF THE DRAWINGS

The accompanying drawings illustrate some objectives, advantages, and a preferred mode of making and using some embodiments of the claimed subject matter. Like reference numbers represent like parts in the examples.

DESCRIPTION OF EXAMPLE EMBODIMENTS

The following description of example embodiments provides information that enables a person skilled in the art to make and use the subject matter set forth in the appended claims, but it may omit certain details already well known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive an implant. However, as should be recognized by those skilled in the art, this frame of reference is merely a descriptive expedient rather than a strict prescription.

Figure 1:
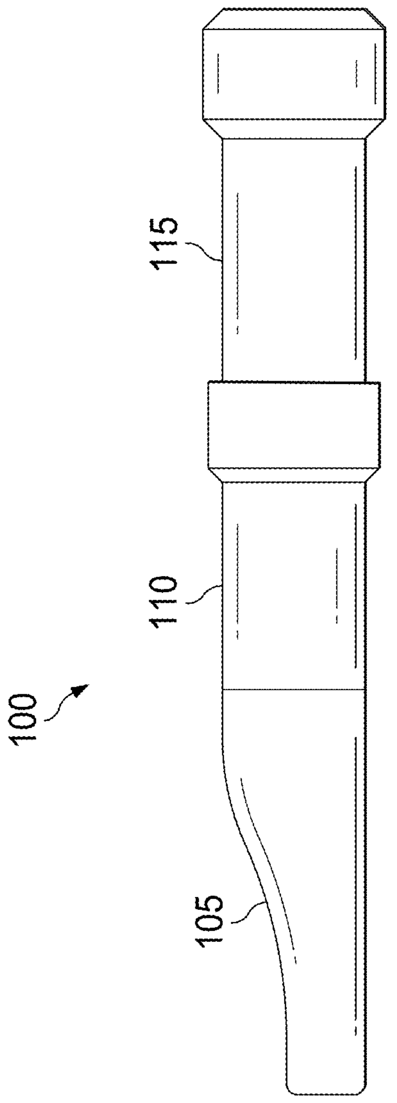
FIG. 1 is a schematic diagram of an example apparatus for inserting an implant into an eye.

FIG. 1 is a schematic diagram of an apparatus 100 that can be used to deliver an implant into an eye. For example, as illustrated in FIG. 1, some embodiments of the apparatus 100 may include a nozzle 105, an implant bay 110 that can be coupled to the nozzle 105, and an actuator 115 that can be coupled to the implant bay 110. In the example of FIG. 1, the nozzle 105, the implant bay 110, and the actuator 115 are fixed together to form a unitary structure. In other examples, the apparatus 100 may comprise two or more modules, which can be configured to be coupled and decoupled as appropriate for storage, assembly, use, and disposal.

The nozzle 105 generally comprises a tip adapted for insertion through an incision into an eye. The size of the tip may be adapted to surgical requirements and techniques as needed. For example, small incisions are generally preferable to reduce or minimize healing times. Incisions of less than 3 millimeters may be preferable in some instances, and the tip of the nozzle 105 may have a width of less than 3 millimeters in some embodiments.

The implant bay 110 generally represents a wide variety of apparatuses that are suitable for storing an implant prior to delivery into an eye. In some embodiments, the implant bay 110 may additionally or alternatively be configured to prepare an implant for delivery. For example, some embodiments of the implant bay 110 may be configured to be actuated by a surgeon or other operator to prepare an implant for delivery by subsequent action of the actuator 115. In some instances, the implant bay 110 may be configured to actively deform, elongate, extend, or otherwise manipulate features of the implant before the implant is advanced into the nozzle 105. For example, the implant bay 110 may be configured to extend or splay one or more features, such as haptics, of an intraocular lens.

In general, components of the apparatus 100 may be coupled directly or indirectly. For example, the nozzle 105 may be directly coupled to the implant bay 110 and may be indirectly coupled to the actuator 115 through the implant bay 110. Coupling may include fluid, mechanical, thermal, electrical, or chemical coupling (such as a chemical bond), or some combination of coupling in some contexts. For example, the actuator 115 may be mechanically coupled to the implant bay 110 and may be mechanically and fluidly coupled to the nozzle 105. In some embodiments, components may also be coupled by virtue of physical proximity, being integral to a single structure, or being formed from the same piece of material.

Figure 2:
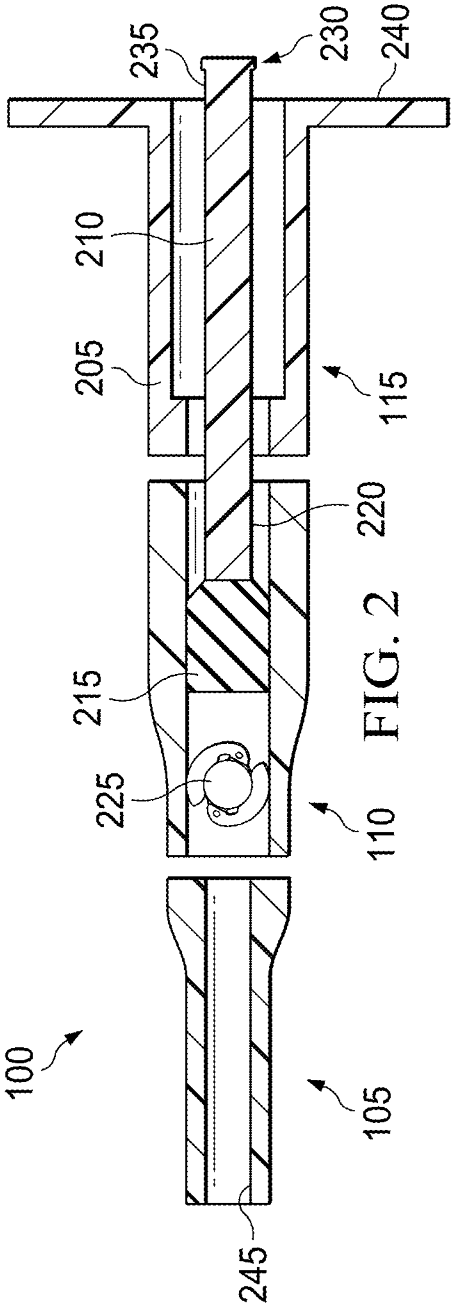
FIG. 2 is a schematic diagram of an example of the apparatus of FIG. 1.

FIG. 2 is a schematic diagram of an example of the apparatus 100 of FIG. 1, illustrating additional details that may be associated with some embodiments. The actuator 115 of FIG. 2 generally comprises a housing 205, a plunger 210 disposed within the housing 205, and a seal 215 coupled to a first end 220 of the plunger 210. The plunger 210 generally comprises a rod or shaft of substantially rigid material, such as a medical grade polymer material, and is configured to slide within the housing 205. The seal 215 is generally configured to move with the plunger 210 and to provide a fluid seal between the implant bay 110 and the plunger 210. The seal 215 may comprise or consist essentially of a soft, compressible material, which can fill the inside of the housing 205 to form the fluid seal. For example, the seal 215 may comprise a thermoplastic elastomer in some embodiments. In some examples, an implant 225 may be stored in the implant bay 110. The actuator 115 may additionally comprise a coupling 230 proximate to a second end 235 of the plunger 210.

Some embodiments of the apparatus 100 may additionally include various ergonomic features. For example, the apparatus 100 of FIG. 2 has a finger flange 240 coupled to the actuator 115, which can facilitate one-handed manipulation of the apparatus 100.

The actuator 115 is generally configured to advance the implant 225 from the implant bay 110 into the nozzle 105, and thereafter from the nozzle 105 through an incision and into an eye. For example, in FIG. 2 the plunger 210 may advance the seal 215 until it contacts the implant 225 in the implant bay 110. The plunger 210 may advance the seal 215 further to move the implant 225 into a delivery lumen 245 in the nozzle 105, and thereafter eject the implant 225 from the delivery lumen 245. In other examples, the implant 225 may be disposed within a working fluid (not shown) in the implant bay 110 and advancing the seal 215 may advance the working fluid and the implant 225 without directly contacting the implant 225.

Figure 3A:
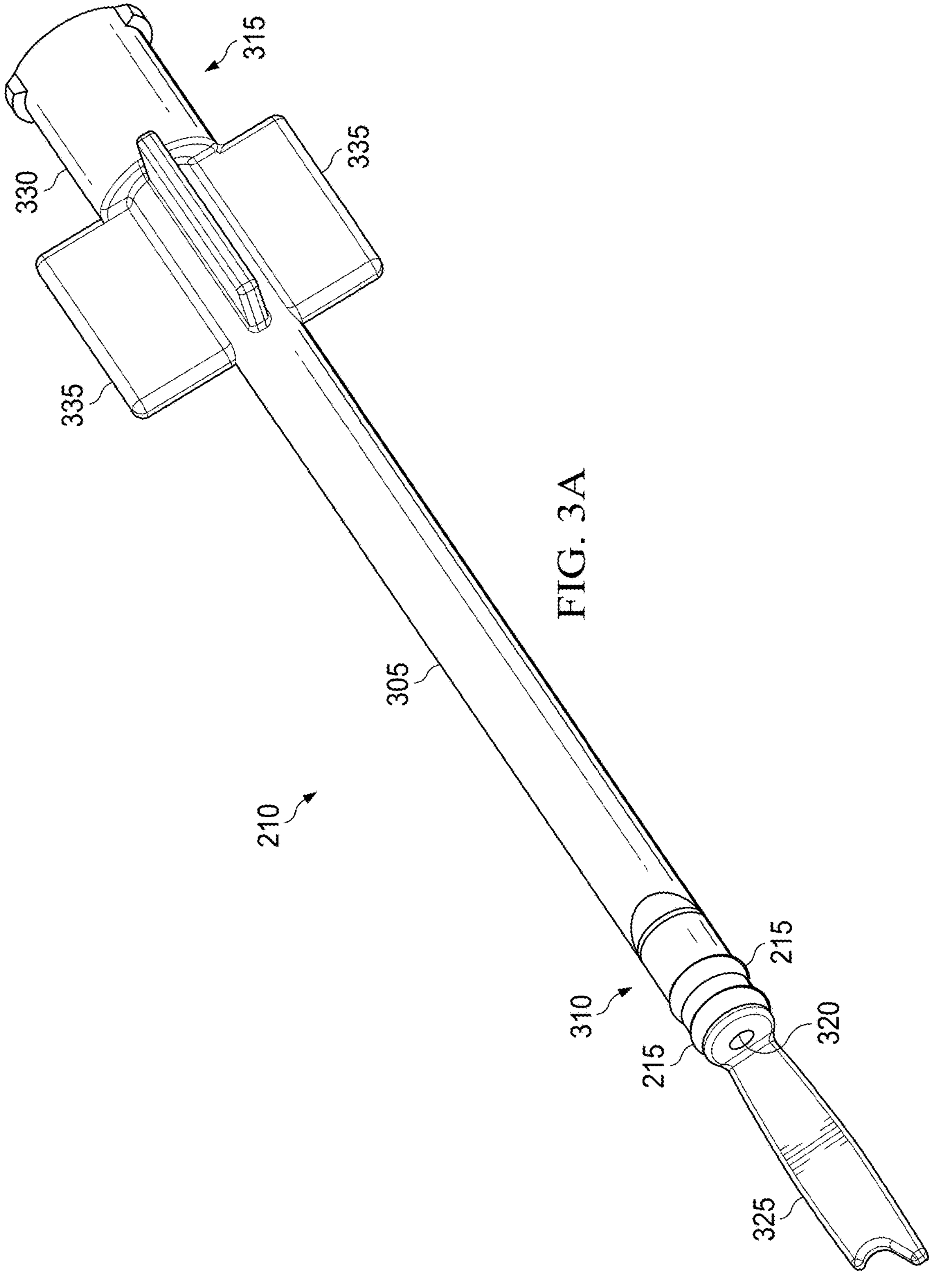
FIG. 3A is an isometric view of another example of a plunger that may be associated with the apparatus of FIG. 1.

FIG. 3A is an isometric view of another example of the plunger 210, illustrating additional details that may be associated with some embodiments. For example, the plunger 210 of FIG. 3A comprises a shaft 305 having a first end 310, a second end 315, and a bore 320 through the shaft 305. The plunger 210 may also have an implant interface 325 proximate to the first end 310 and a fluid coupling 330 proximate to the second end 315. Some embodiments of the fluid coupling 330 may comprise or consist essentially of a luer lock fitting, as illustrated in the example of FIG. 3A. One or more guide fins may be coupled to the shaft 305 in some embodiments. For example, the plunger 210 of FIG. 3A comprises a plurality of guide fins 335 disposed radially around the shaft 305 between the first end 310 and the second end 315. In FIG. 3A, the guide fins 335 are disposed between the first end 310 and the fluid coupling 330.

Figure 3B:
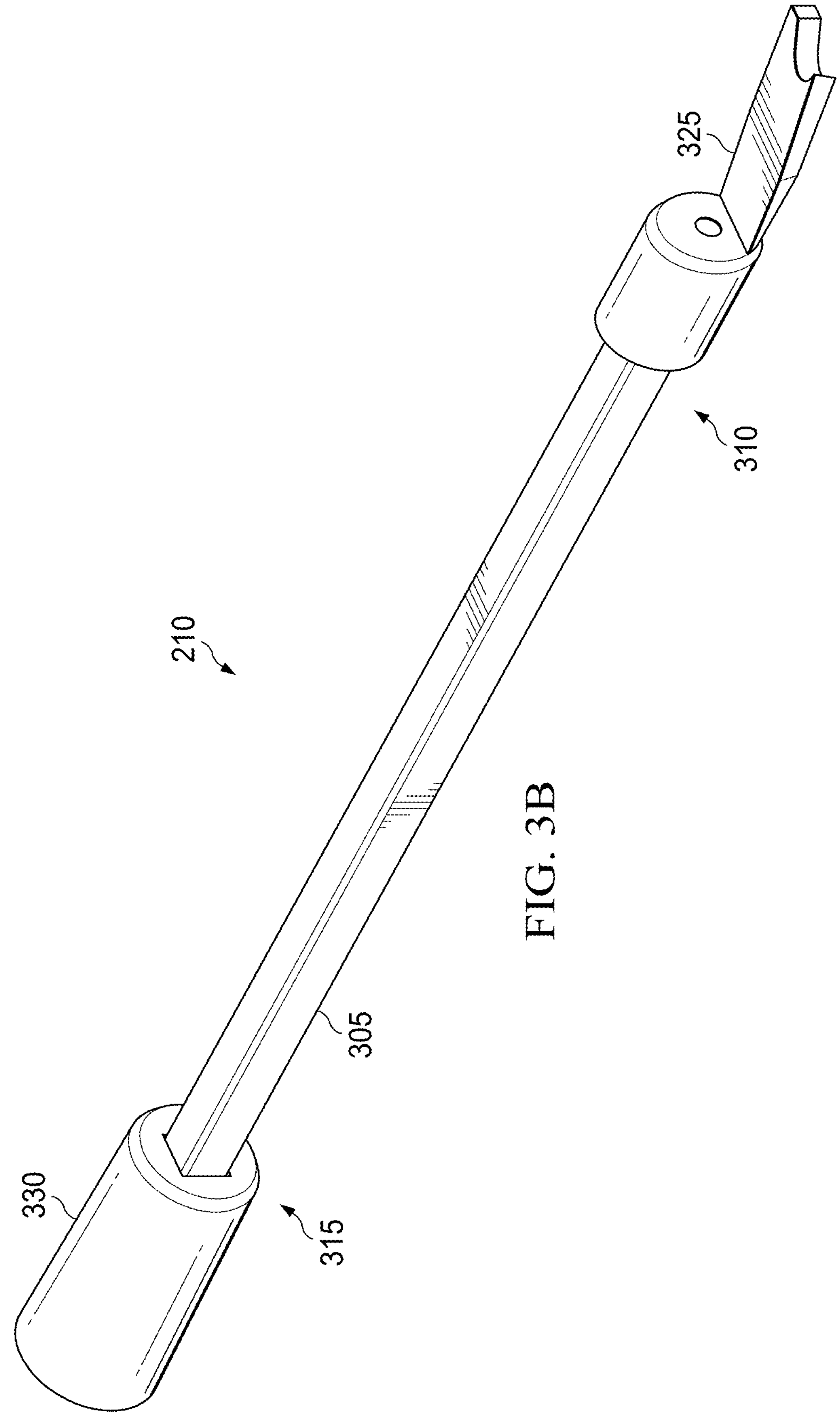
FIG. 3B is an isometric view of another example of a plunger that may be associated with the apparatus of FIG. 1.

FIG. 3B is an isometric view of another example of the plunger 210 that may be associated with the apparatus of FIG. 1, illustrating additional details that may be associated with some embodiments. For example, FIG. 3B illustrates an embodiment of the plunger 210 in which the shaft 305 has a rectangular (or square) section. In some examples, the first end 310 of the shaft 305 may be inserted into the implant interface 325, and the second end 315 may be inserted into the fluid coupling 330. As illustrated in the example of FIG. 3B, some embodiments of the fluid coupling 330 may comprise or consist essentially of a luer slip fitting.

Figure 4A:
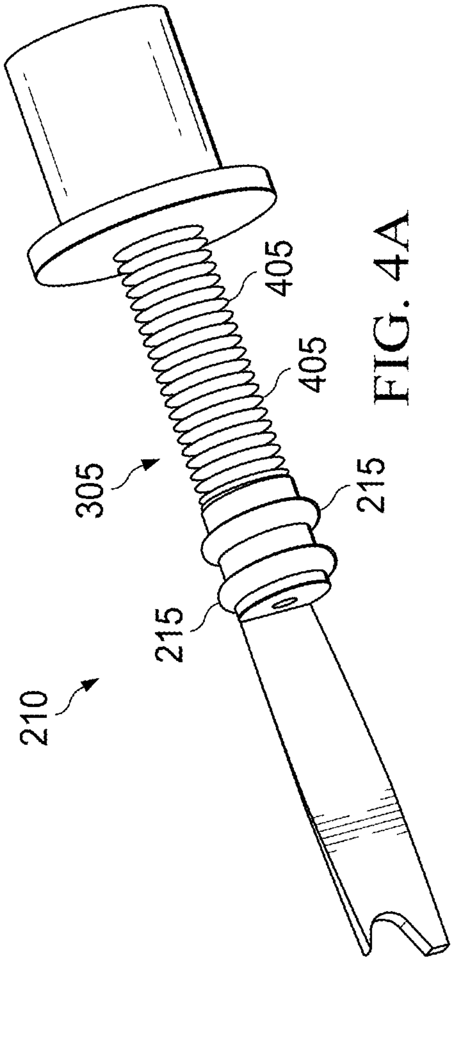
FIG. 4A and FIG. 4B are isometric views of another example of a plunger that may be associated with the apparatus of FIG. 1.
Figure 4B:
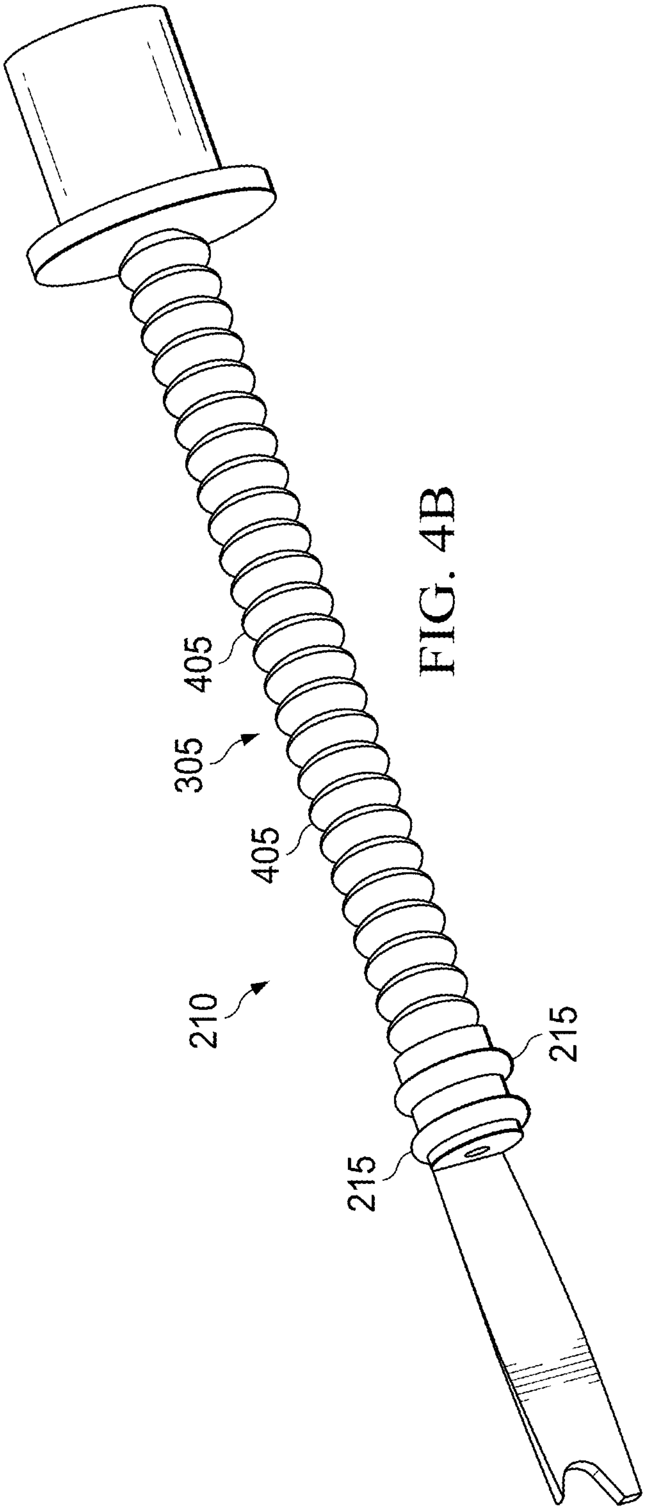

FIG. 4A and FIG. 4B are isometric views of another example of the plunger 210, illustrating additional details that may be associated with some embodiments. For example, the shaft 305 of FIG. 4A is extendable. FIG. 4A illustrates the shaft 305 in a compressed or retracted configuration, and FIG. 4B illustrates the shaft 305 in an expanded or extended configuration. In some embodiments, the shaft 305 may have articulated sections. More particularly, the shaft 305 of FIG. 4A and FIG. 4B comprises at least two concertinaed sections 405, each of which may comprise flexible sidewalls configured allow the sections 405 to extend and retract.

Figure 5A:
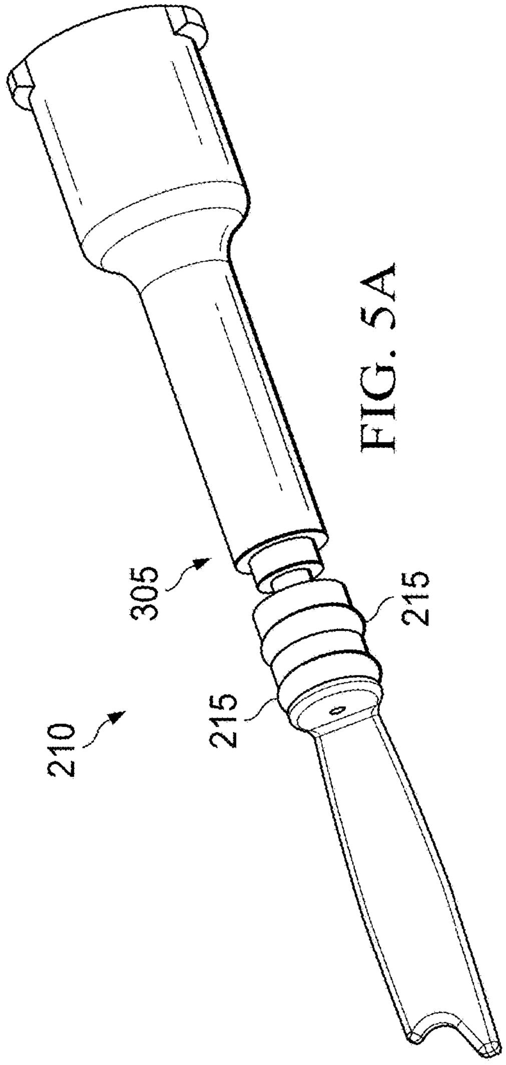
FIG. 5A and FIG. 5B are isometric views of another example of a plunger that may be associated with the apparatus of FIG. 1.
Figure 5B:
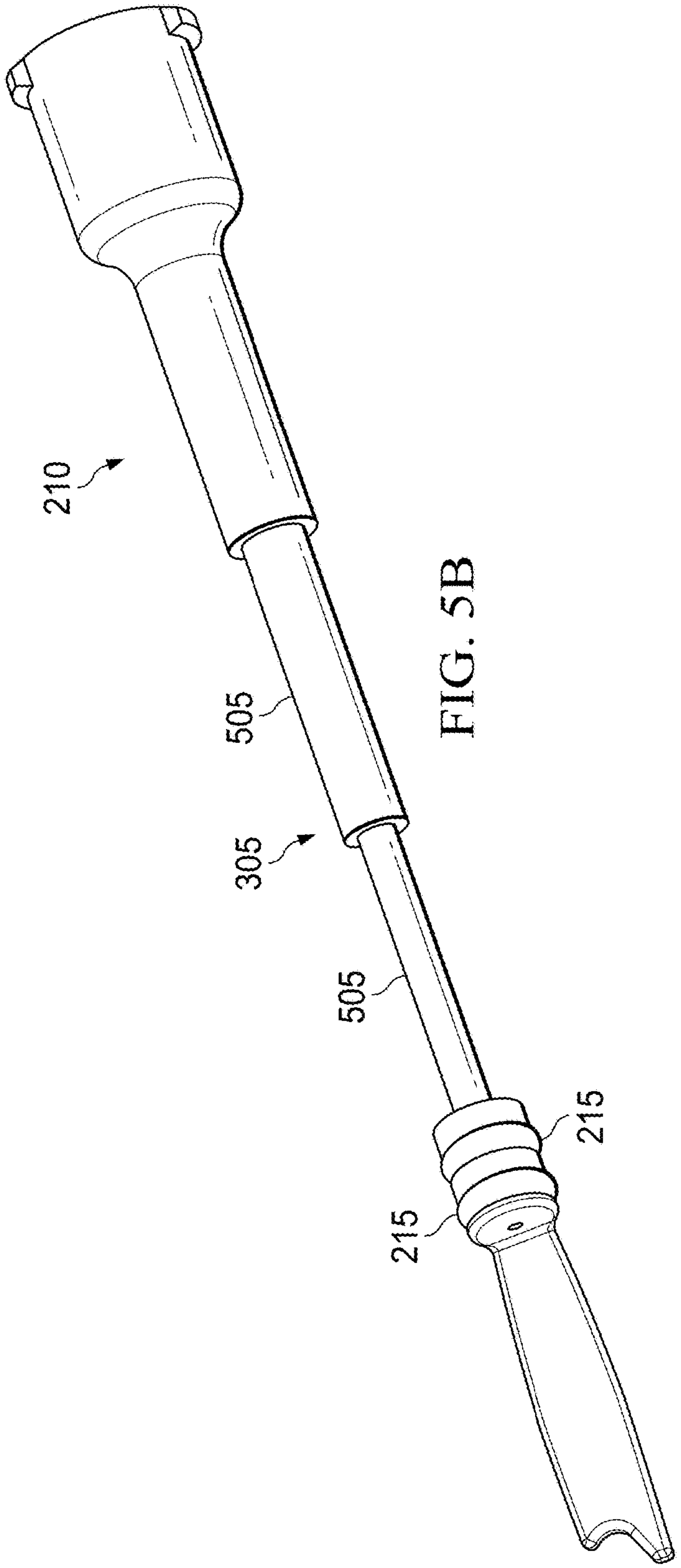

FIG. 5A and FIG. 5B are isometric views of another example of the plunger 210, illustrating additional details that may be associated with some examples. The shaft 305 of FIG. 5A is extendable. FIG. 5A illustrates the shaft 305 in a compressed or retracted configuration, and FIG. 5B illustrates the shaft 305 in an expanded or extended configuration. In some embodiments, the shaft 305 may have articulated sections. More particularly, the shaft 305 of FIG. 5A and FIG. 5B comprises at least two telescoping sections 505.

FIG. 6A, FIG. 6B, FIG. 6C, and FIG. 6D are schematic diagrams illustrating an example operation of the apparatus 100 with the plunger 210 of FIG. 3A. Initially, various components of the apparatus 100 may be assembled if appropriate.

Figure 6A:
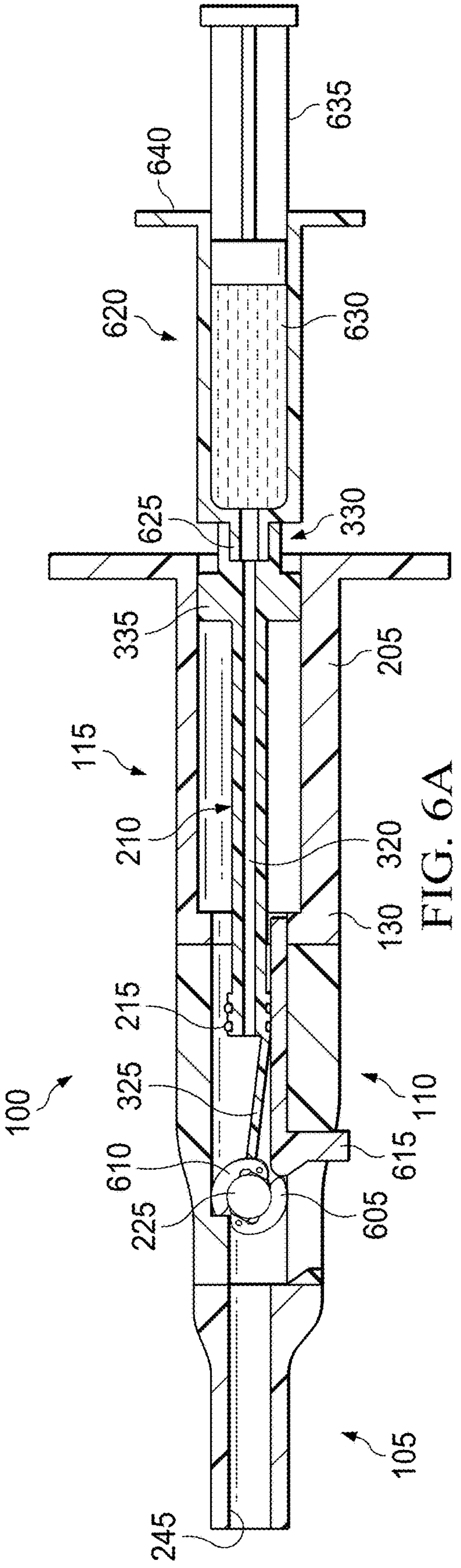
FIG. 6A, FIG. 6B, FIG. 6C, and FIG. 6D are schematic diagrams illustrating an example operation of the apparatus of FIG. 1.

If assembled as illustrated in FIG. 6A, the implant bay 110 may be disposed between the bore 320 and the delivery lumen 245. The implant 225 may be provided in the implant bay 110, as illustrated in the example of FIG. 6A. In some embodiments, the implant 225 may comprise or consist essentially of an intraocular lens having a shape similar to that of a natural lens of an eye, and it may be made from numerous materials. Examples of suitable materials may include silicone, acrylic, or combinations of such suitable materials. In some instances, the implant 225 may comprise or consist essentially of an intraocular lens that is filled with a fluid, such as an accommodating intraocular lens.

Figure 6B:
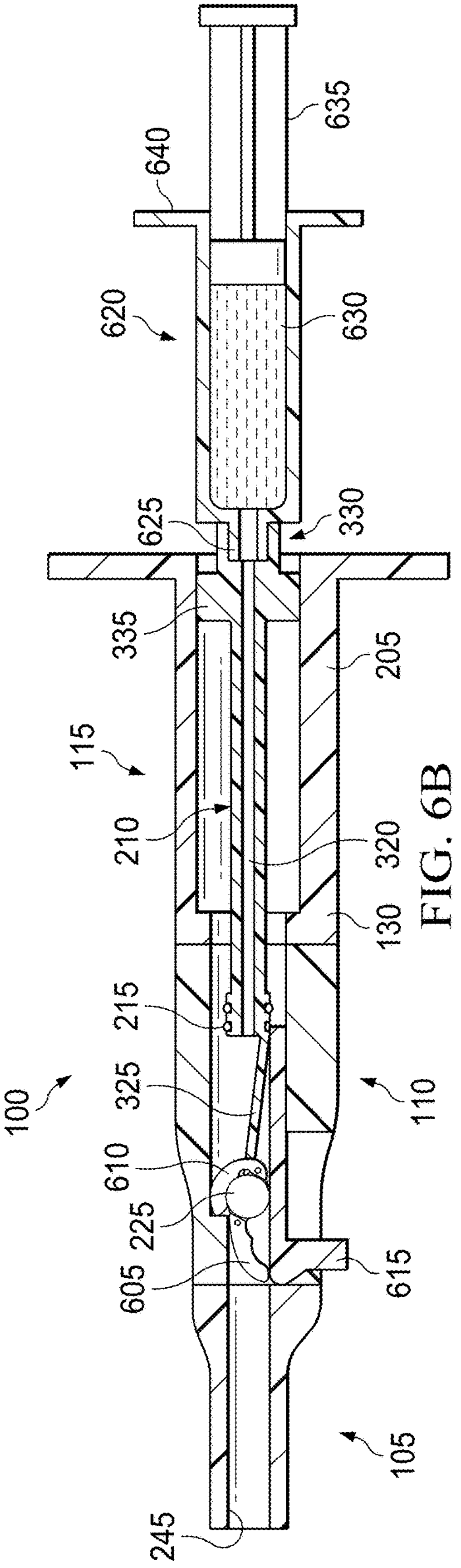

The implant 225 may also comprise one or more features for positioning the implant 225 within an eye. For example, the implant 225 of FIG. 6A comprises a leading haptic 605 and a trailing haptic 610. In some embodiments, the implant bay 110 may be configured to splay or orient one or more of the leading haptic 605 and the trailing haptic 610 for delivery. In some embodiments, the implant bay 110 comprises a splay arm 615 configured to actively splay the leading haptic 605. As illustrated in FIG. 6A and FIG. 6B, for example, the splay arm 615 may be advanced toward the nozzle 105 to splay the leading haptic 605.

In the example of FIG. 6A, the apparatus 100 is configured to receive a hydraulic driver 620. The hydraulic driver 620 of FIG. 6A generally comprises a drive coupling 625, a working fluid 630, and a drive plunger 635. In some embodiments, the hydraulic driver 620 may comprise or consist essentially of a vial of working fluid. Suitable working fluids may include, for example, a saline or a viscous lubricant with non-Newtonian properties.

The fluid coupling 330 may be configured to receive the hydraulic driver 620 and to fluidly couple the working fluid 630 in the hydraulic driver 620 to the bore 320. For example, the drive coupling 625 may be configured to be coupled to the fluid coupling 330. In some embodiments, the fluid coupling 330 may be a luer lock, luer slip, or similar fitting configured to receive the drive coupling 625. For example, the fluid coupling 330 may comprise a male luer lock having at least one locking tab, and the drive coupling 625 may comprise a female luer lock configured to receive the locking tab.

A portion of the plunger 210 and the implant interface 325 may extend into the implant bay 110, and the implant interface 325 may be configured to engage the implant 225. The plunger 210 is generally configured to advance the implant 225 from the implant bay 110 into the delivery lumen 245 of the nozzle 105. For example, if the drive coupling 625 is coupled to the fluid coupling 330, force can be applied to the hydraulic driver 620 to move the hydraulic driver 620 and the plunger 210 within the housing 205 from an initial configuration illustrated in the example of FIG. 6B to another configuration illustrated in the example of FIG. 6C. In some embodiments, the hydraulic driver 620 may comprise a flange 640, and pressure can be applied to the flange 640 to rigidly move the hydraulic driver 620 and the plunger 210 to the second configuration while maintaining the relative position of the drive plunger 635 and the working fluid 630. The guide fins 335 may be configured to maintain the orientation of the plunger 210 as it moves within the housing 205. In some embodiments, the nozzle 105, the implant bay 110, or both may comprise features to passively splay the trailing haptic 610. For example, the implant bay 110 of FIG. 6B may passively engage the trailing haptic 610 as the plunger 210 advances the implant 225 into the delivery lumen 245 so that the trailing haptic 610 is splayed within the delivery lumen 245, as illustrated in FIG. 6C.

Figure 6C:
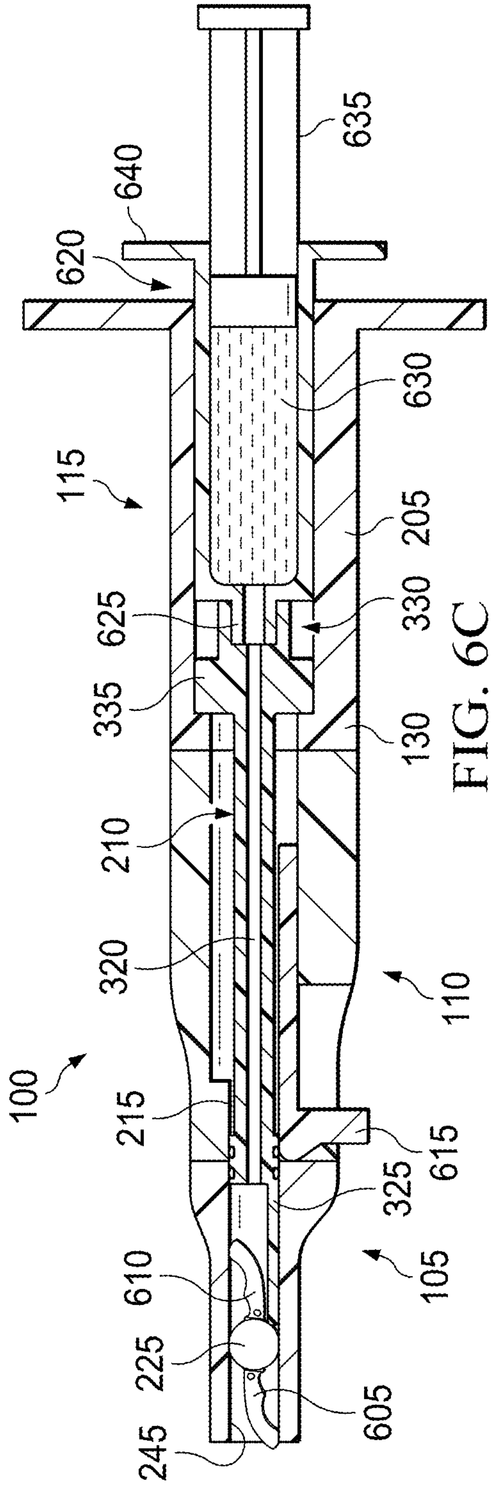

In the second configuration illustrated in FIG. 6C, the seal 215 is also advanced into the delivery lumen 245 to create a seal in the delivery lumen 245 behind the implant 225. The implant 225 may also form a seal with the delivery lumen 245 in some instances. In general, the bore 320 may extend between the first end 310 of the shaft 305 and the second end 315 of the shaft 305. In the configuration of FIG. 6C, the bore 320 may fluidly couple the working fluid 630 in the hydraulic driver 620 to the delivery lumen 245.

Figure 6D:
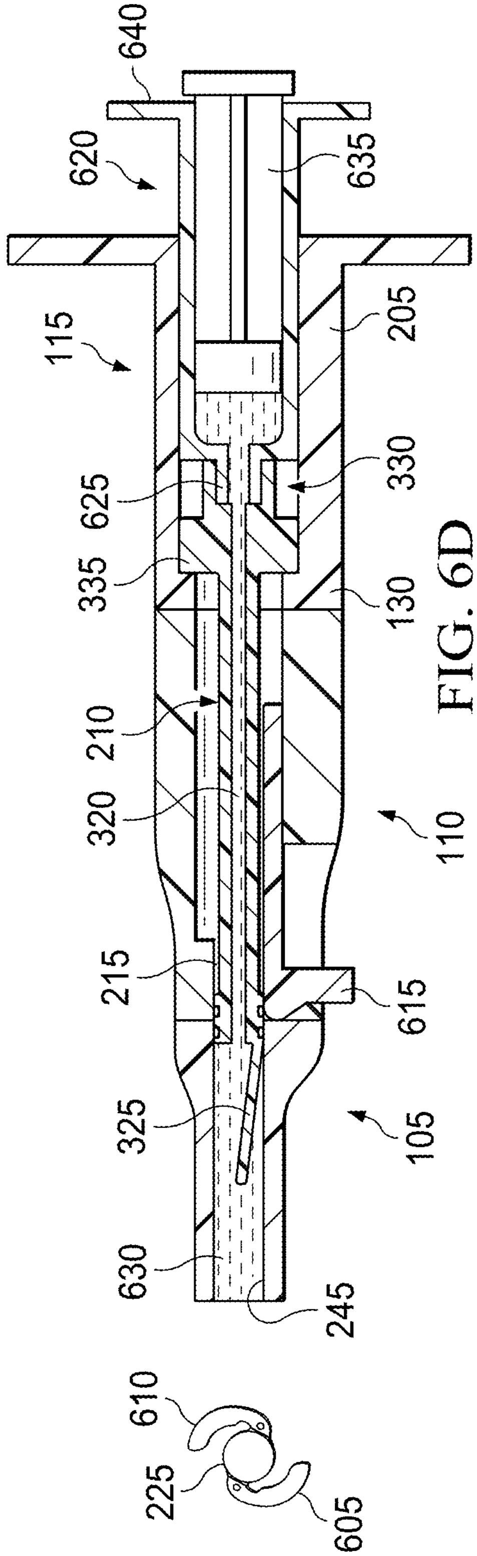

In the configuration of FIG. 6C, the drive plunger 635 may be advanced to a third configuration, as illustrated in the example of FIG. 6D, forcing the working fluid 630 through the bore 320 into the delivery lumen 245 behind the implant 225. Movement of the working fluid 630 from the bore 320 into the delivery lumen 245 under pressure from the drive plunger 635 can increase the pressure and flow rate of the working fluid 630 in the delivery lumen 245 behind the implant 225, which can advance the implant 225 further through the delivery lumen 245 until the implant 225 is ejected from the nozzle 105.

FIG. 7A, FIG. 7B, FIG. 7C, and FIG. 7D are schematic diagrams illustrating an example operation of the apparatus 100 with the plunger 210 of FIG. 4A and FIG. 4B. Initially, various components of the apparatus 100 may be assembled if appropriate.

Figure 7A:
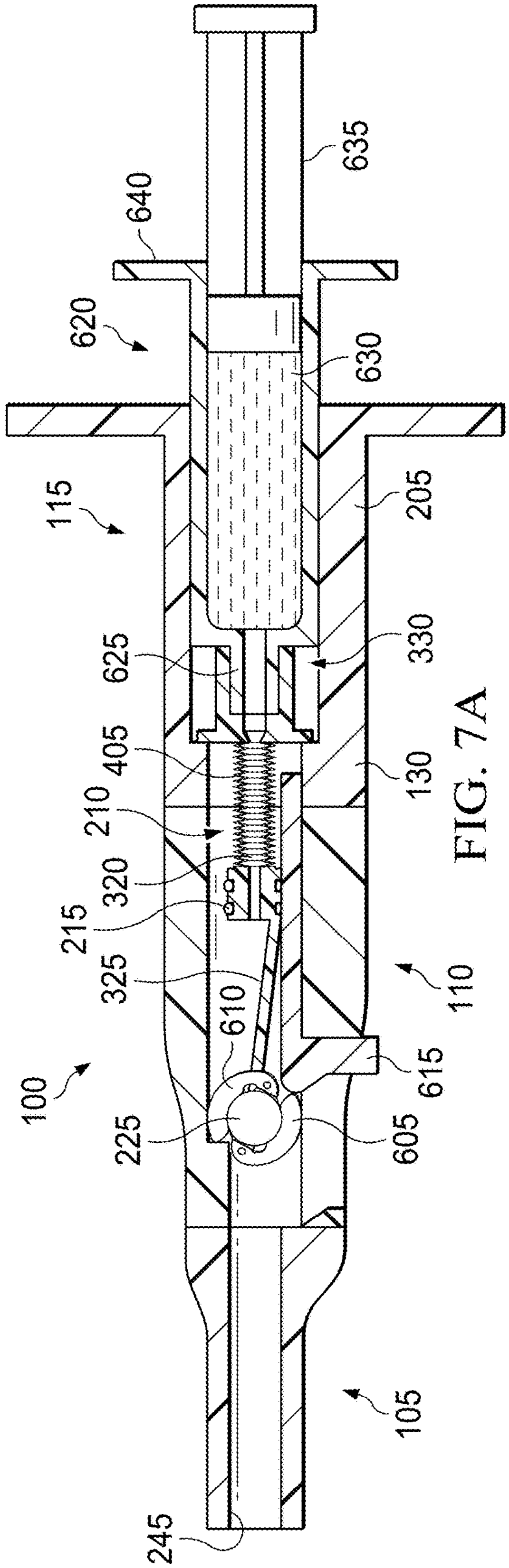
FIG. 7A, FIG. 7B, FIG. 7C, and FIG. 7D are schematic diagrams illustrating another example operation of the apparatus of FIG. 1.

In the example of FIG. 7A, the apparatus 100 is configured to receive a hydraulic driver, such as the hydraulic driver 620 of FIG. 6A.

The plunger 210 is generally configured to advance the implant 225 from the implant bay 110 into the delivery lumen 245 of the nozzle 105. For example, if the drive coupling 625 is coupled to the fluid coupling 330, force can be applied to the hydraulic driver 620 to move the hydraulic driver 620 and the plunger 210 within the housing 205 to the first configuration illustrated in FIG. 7A. A portion of the plunger 210 and the implant interface 325 may extend into the implant bay 110, and the implant interface 325 may be configured to engage the implant 225.

Figure 7B:
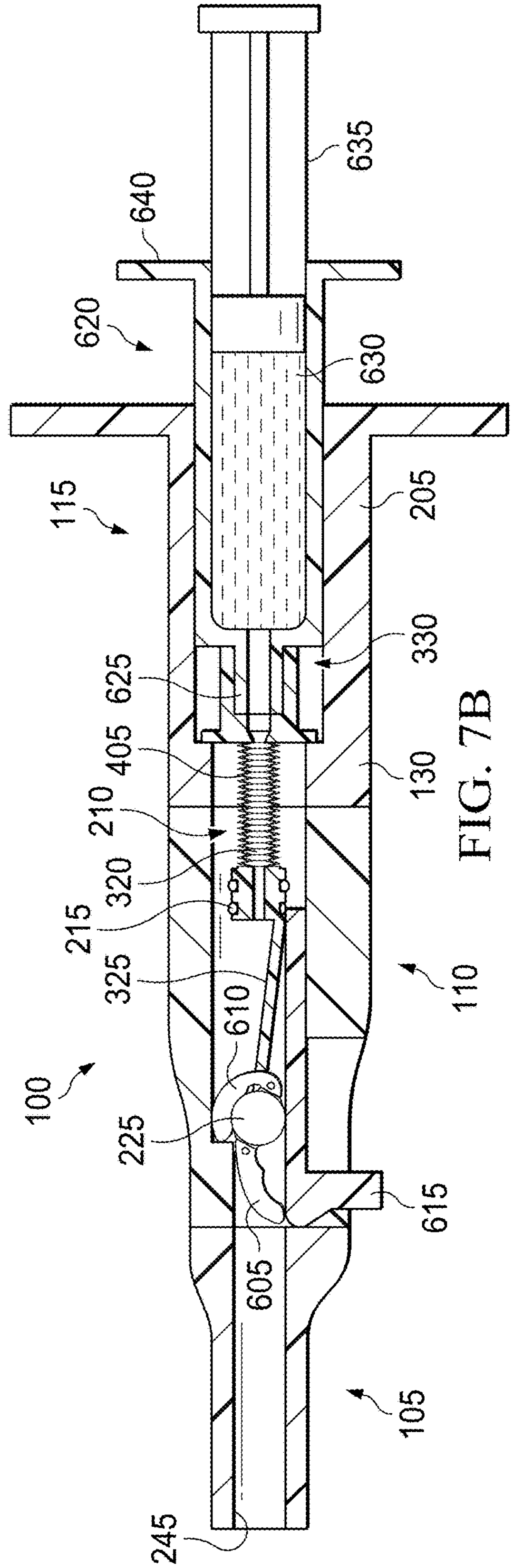
Figure 7C:
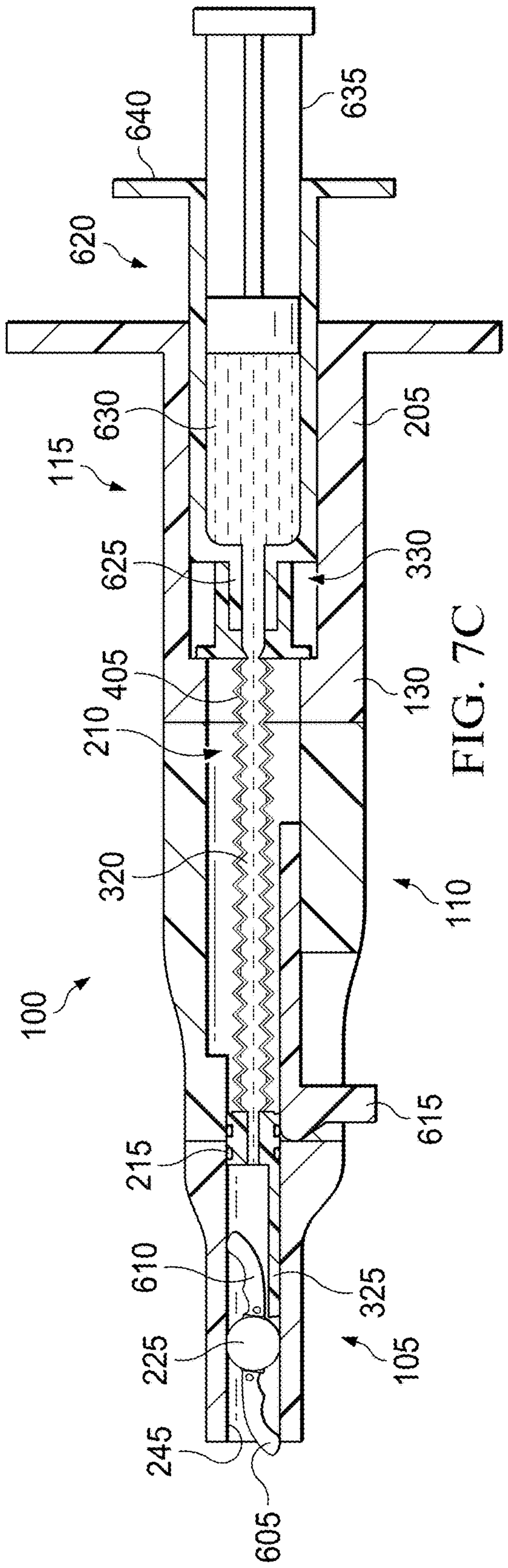

From the configuration of FIG. 7A, the splay arm 615 may be advanced toward the nozzle 105 to splay the leading haptic 605, as illustrated in the example of FIG. 7B. The drive plunger 635 may be advanced to a second configuration, as illustrated in the example of FIG. 7C, which can force the working fluid 630 into the bore 320. The bore 320 can reduce the flow rate of the working fluid 630 and increase the pressure of the working fluid 630. Movement of the working fluid 630 under pressure into the bore 320 can cause the concertinaed sections 405 to extend the shaft 305 into a second configuration, as illustrated in the example configuration of FIG. 7C.

Figure 7D:
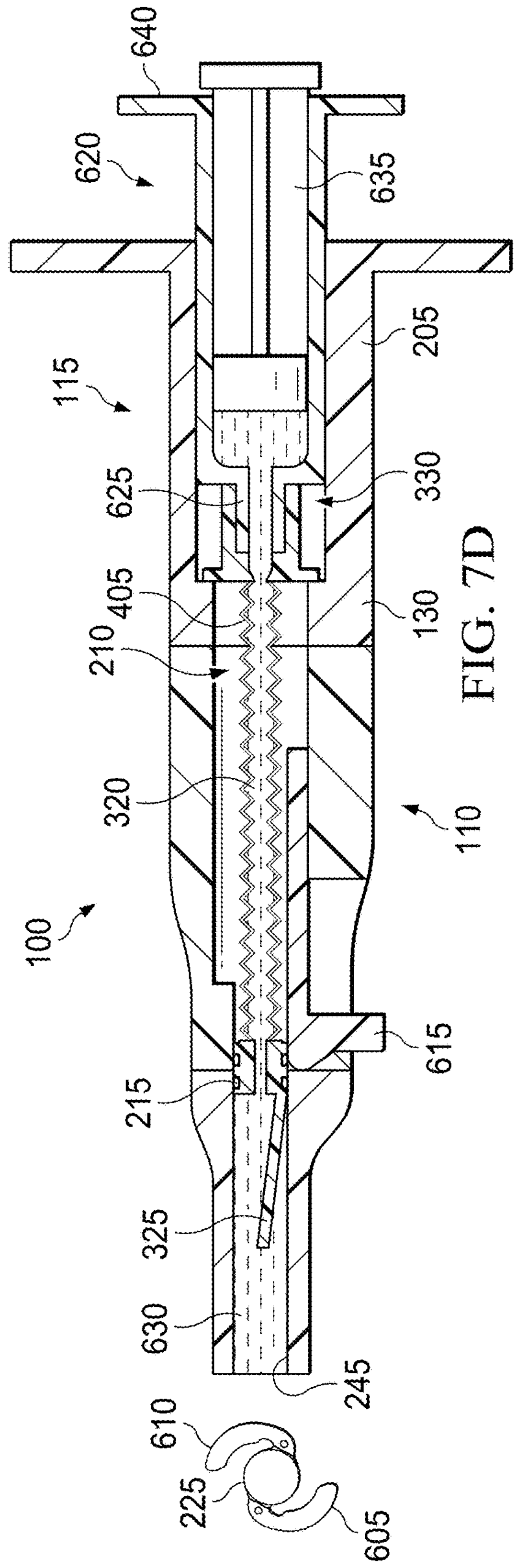

In the configuration of FIG. 7C, the drive plunger 635 may be advanced to a third configuration, as illustrated in the example of FIG. 7D, forcing the working fluid 630 through the bore 320 into the delivery lumen 245 behind the implant 225. Movement of the working fluid 630 from the bore 320 into the delivery lumen 245 under pressure from the drive plunger 635 can increase the pressure and flow rate of the working fluid 630 in the delivery lumen 245 behind the implant 225, which can advance the implant 225 further through the delivery lumen 245 until the implant 225 is ejected from the nozzle 105.

FIG. 8A, FIG. 8B, FIG. 8C, and FIG. 8D are schematic diagrams illustrating an example operation of the apparatus 100 with the plunger 210 of FIG. 5A and FIG. 5B. Initially, various components of the apparatus 100 may be assembled if appropriate.

Figure 8A:
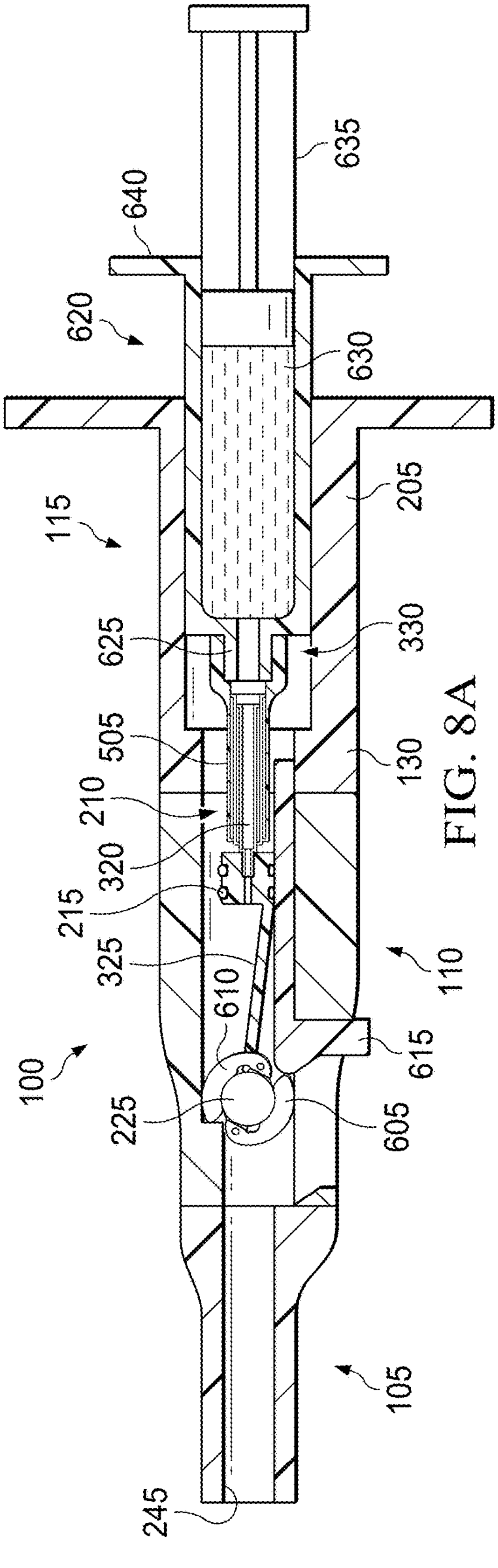
FIG. 8A, FIG. 8B, FIG. 8C, and FIG. 8D are schematic diagrams illustrating another example operation of the apparatus of FIG. 1.

In the example of FIG. 8A, the apparatus 100 is configured to receive a hydraulic driver, such as the hydraulic driver 620 of FIG. 6A.

The plunger 210 is generally configured to advance the implant 225 from the implant bay 110 into the delivery lumen 245 of the nozzle 105. For example, if the drive coupling 625 is coupled to the fluid coupling 330, force can be applied to the hydraulic driver 620 to move the hydraulic driver 620 and the plunger 210 within the housing 205 to the first configuration illustrated in FIG. 8A. A portion of the plunger 210 and the implant interface 325 may extend into the implant bay 110, and the implant interface 325 may be configured to engage the implant 225.

Figure 8B:
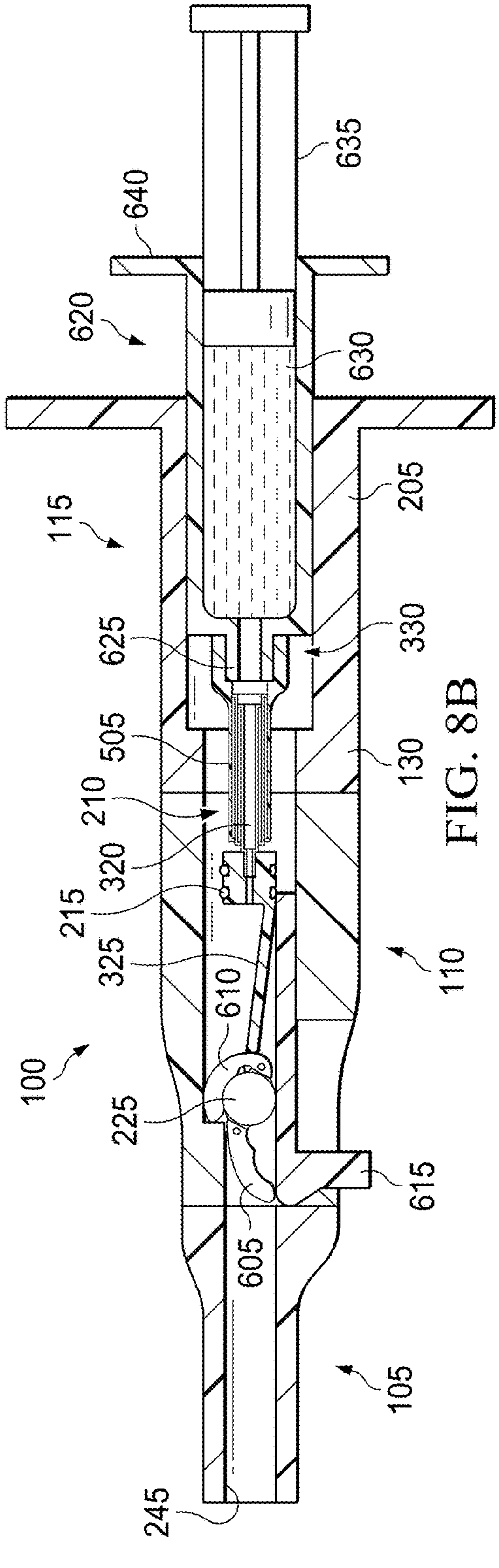
Figure 8C:
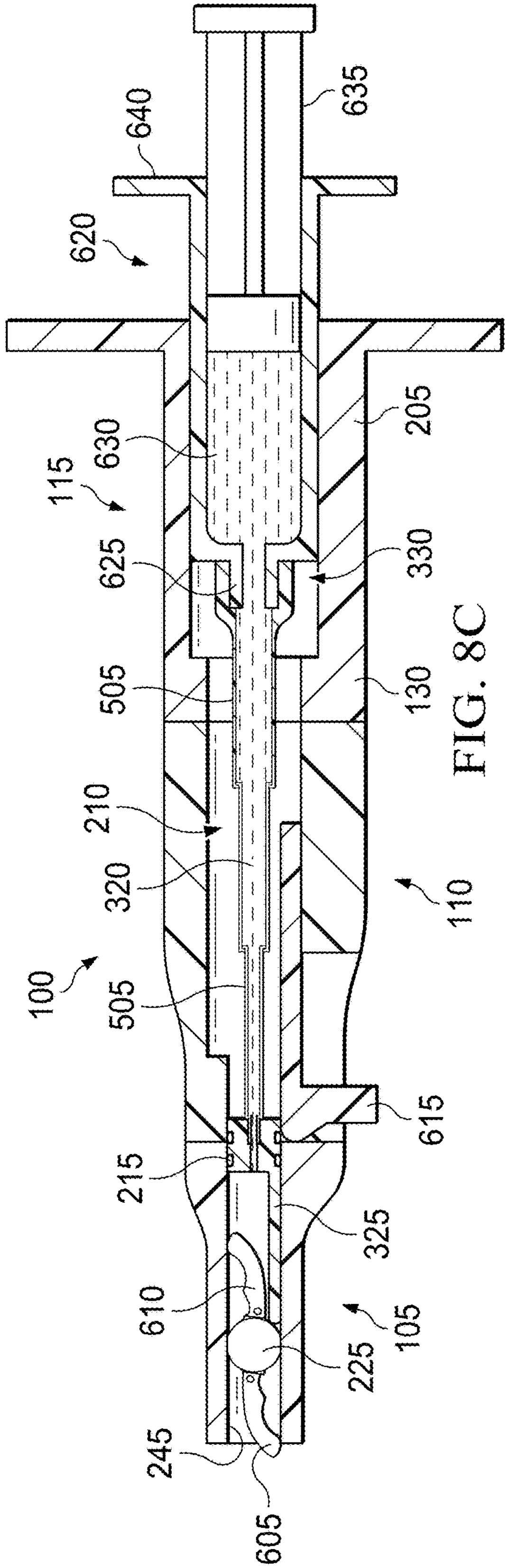

From the configuration of FIG. 8A, the splay arm 615 may be advanced toward the nozzle 105 to splay the leading haptic 605, as illustrated in the example of FIG. 8B. The drive plunger 635 may be advanced to a second configuration, as illustrated in the example of FIG. 8C, which can force the working fluid 630 into the bore 320. The bore 320 can reduce the flow rate of the working fluid 630 and increase the pressure of the working fluid 630. Movement of the working fluid 630 under pressure into the bore 320 can cause the telescoping sections 505 to extend the shaft 305 into a second configuration, as illustrated in the example configuration of FIG. 8C.

Figure 8D:
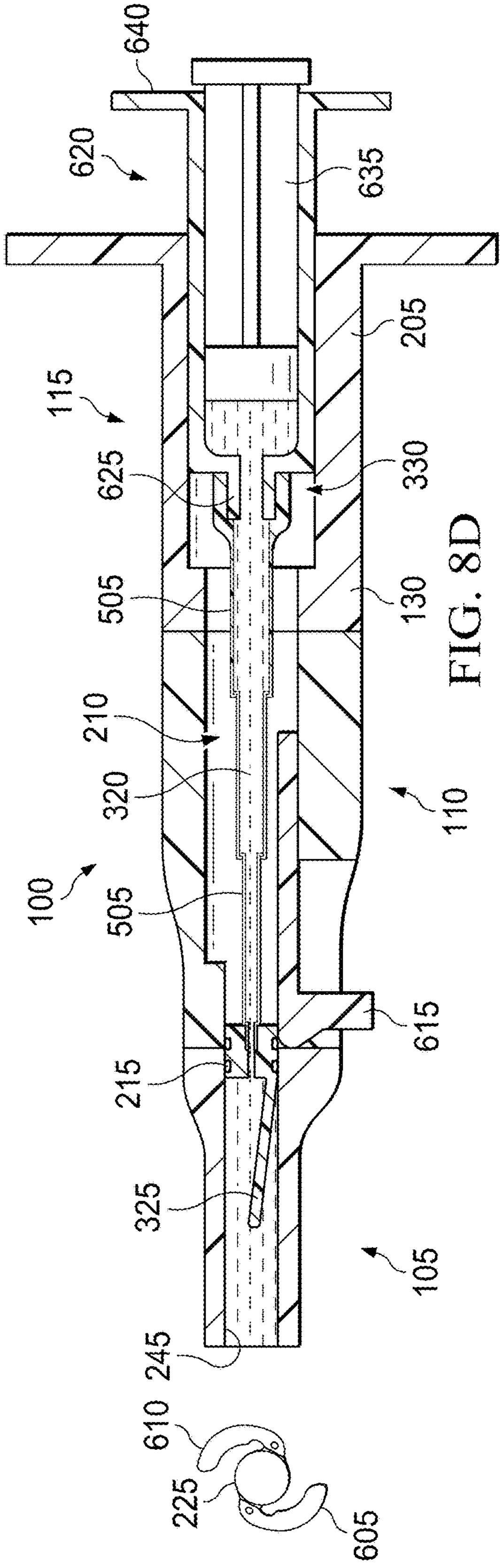

From the configuration of FIG. 8C, the drive plunger 635 may be advanced to a third configuration, as illustrated in the example of FIG. 8D, forcing the working fluid 630 through the bore 320 into the delivery lumen 245 behind the implant 225. Movement of the working fluid 630 from the bore 320 into the delivery lumen 245 under pressure from the drive plunger 635 can increase the pressure and flow rate of the working fluid 630 in the delivery lumen 245 behind the implant 225, which can advance the implant 225 further through the delivery lumen 245 until the implant 225 is ejected from the nozzle 105.

Figure 9A:
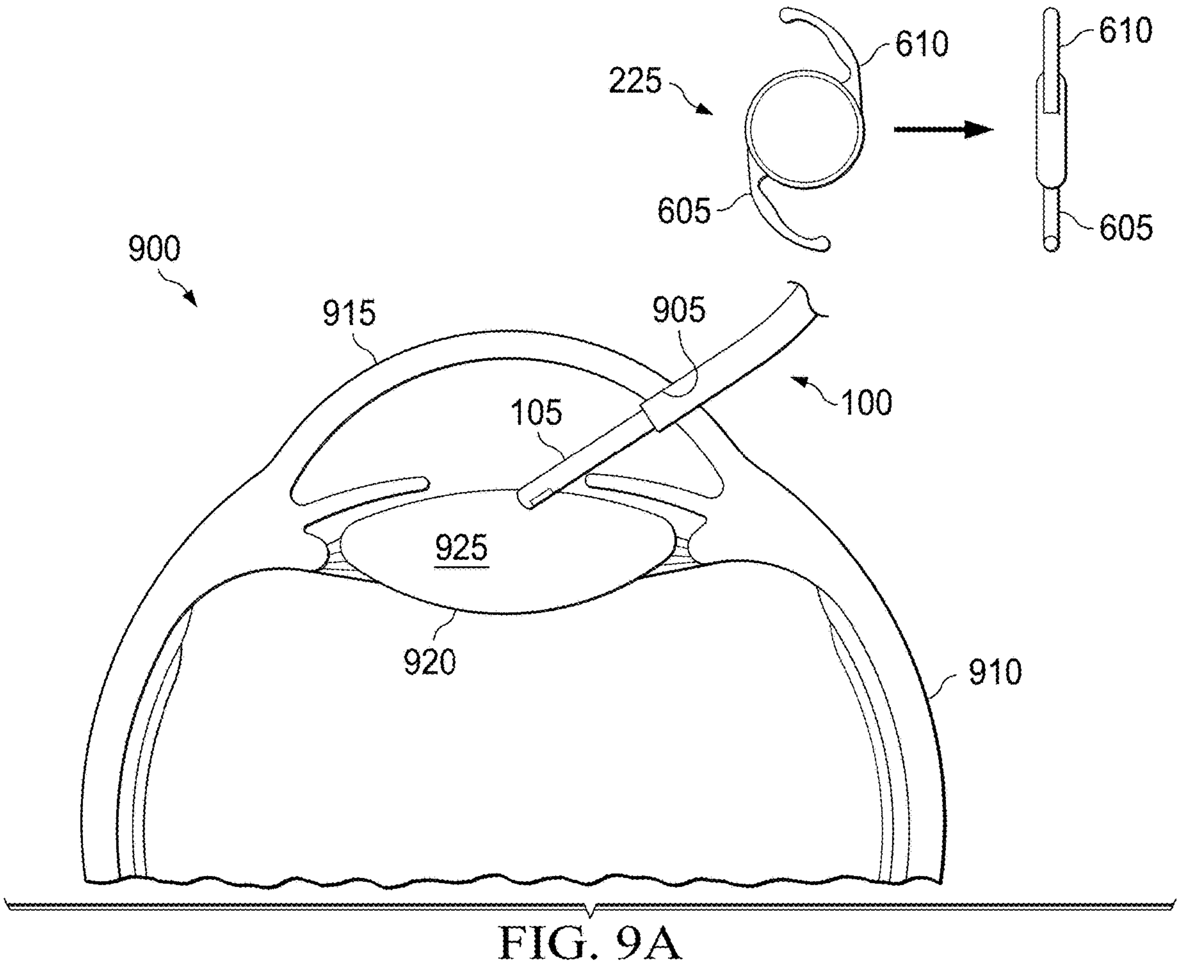
FIG. 9A and FIG. 9B are schematic diagrams further illustrating an example use of the apparatus of FIG. 1 to deliver an implant to an eye.
Figure 9B:
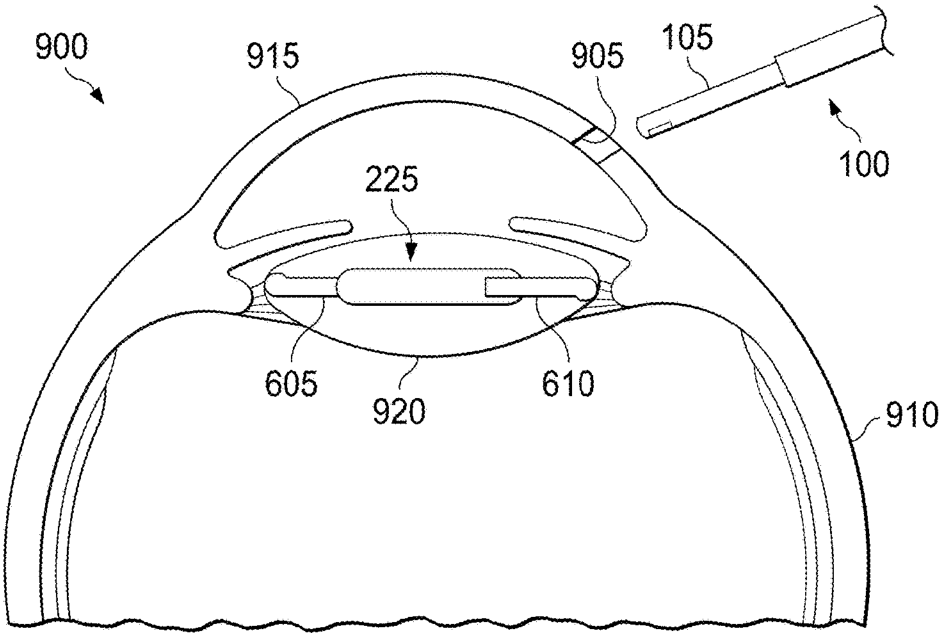

FIG. 9A and FIG. 9B are schematic diagrams further illustrating an example use of the apparatus 100 to deliver the implant 225 to an eye 900. As illustrated, an incision 905 may be made in the eye 900 by a surgeon, for example. In some instances, the incision 905 may be made through the sclera 910 of the eye 900. In other instances, an incision may be formed in the cornea 915 of the eye 900. The incision 905 may be sized to permit insertion of a portion of the nozzle 105 to deliver the implant 225 into the capsular bag 920. For example, in some instances, the size of the incision 905 may have a length less than about 3000 microns (3 millimeters). In other instances, the incision 905 may have a length of from about 1000 microns to about 1500 microns, from about 1500 microns to about 2000 microns, from about 2000 microns to about 2500 microns, or from about 2500 microns to about 3000 microns.

After the incision 905 is made, the nozzle 105 can be inserted through the incision 905 into an interior portion 925 of the eye 900. The apparatus 100 can then eject the implant 225 through the nozzle 105 into the capsular bag 920 of the eye 900, substantially as described above. In some applications, the implant 225 may be delivered in a folded configuration and can revert to an initial, unfolded state, within the capsular bag 920, as shown in FIG. 9B. For example, the implant 125 may be in the form of an accommodating intraocular lens having one or more of the leading haptic 605 and the trailing haptic 610 filled with fluid. The capsular bag 920 can retain the implant 225 within the eye 900 in a relationship relative to the eye 900 so that the implant 225 refracts light directed to the retina (not shown). The leading haptic 605 and the trailing haptic 610 can engage the capsular bag 920 to secure the implant 225 therein. After dispensing the implant 225 into the capsular bag 920, the nozzle 105 may be removed from the eye 900 through the incision 905, and the eye 900 can be allowed to heal over a period of time.

The systems, apparatuses, and methods described herein may provide significant advantages. For example, some embodiments may be particularly advantageous for delivering intraocular lenses, including fluid-filled accommodating lenses, which can present unique challenges for delivery. Some embodiments can compress a relatively large lens to fit through an acceptably small incision, manage deformation caused by shifting fluid during compression and exit from a nozzle, and execute delivery in a predictable and controlled manner. Additionally, some embodiments can reduce system complexity and the number of delivery steps while maintaining haptic position consistency. Some embodiments may also reduce the amount of working fluid for delivery. For example, a single vial of ophthalmic viscosurgical device (OVD), such as vial of CELLUGEL OVD, may be used to drive some embodiments of the apparatus 100 and provide the working fluid for delivery.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context.

Components may be also be combined or eliminated in various configurations for purposes of sale, manufacture, assembly, or use. For example, in some configurations, the nozzle 105, the implant bay 110, and the actuator 115 may each be separated from one another or combined in various ways for manufacture or sale. In other examples, features illustrated in certain examples may be omitted or combined with features illustrated in other examples.

The claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. A plunger for advancing an implant in an implant delivery system, the plunger comprising:
- a shaft having a first end, a second end, and a bore between the first end and the second end;
- an implant interface proximate to the first end and configured to engage the implant; and
- a fluid coupling proximate to the second end and configured to fluidly couple a working fluid to the bore.

2. The plunger of claim 1, further comprising at least one guide fin disposed between the first end and the fluid coupling.

3. The plunger of claim 1, further comprising a plurality of guide fins disposed radially around the shaft between the first end and the fluid coupling.

4. The plunger of claim 1, wherein the shaft is extendable.

5. The plunger of claim 1, wherein the shaft comprises at least two articulated sections.

6. The plunger of claim 1, wherein the shaft comprises at least two concertinaed sections.

7. The plunger of claim 1, wherein the shaft comprises at least two telescoping sections.

8. The plunger of claim 4, wherein the shaft is configured to be extended by the working fluid.

9. An apparatus for ejecting an implant for eye surgery, the apparatus comprising:
- a nozzle having a delivery lumen;
- an implant bay coupled to the nozzle; and
- an actuator coupled to the implant bay, the actuator comprising a housing and a plunger disposed within the housing;
- wherein the plunger comprises a shaft having a first end and a second end, an implant interface configured to advance the implant from the implant bay to the delivery lumen, a bore between the first end and the second end, and a fluid coupling proximate to the second end of the shaft configured to fluidly couple a working fluid to the delivery lumen through the bore to advance the implant through the delivery lumen.

10. A method of ejecting an implant from a delivery system, the method comprising:
- providing the implant in an implant bay;
- coupling a hydraulic driver to a plunger;
- driving the plunger with the hydraulic driver to advance the implant from the implant bay to a delivery lumen;
- pressing a working fluid from the hydraulic driver to move the working fluid through a bore in the plunger to the delivery lumen; and
- advancing the implant through the delivery lumen with the working fluid.

11. The method of claim 10, wherein driving the plunger comprises extending the plunger by pressing the working fluid from the hydraulic driver through the bore.

12. An apparatus for eye surgery, the apparatus comprising:
- a nozzle having a delivery lumen;
- an implant bay coupled to the nozzle;
- a working fluid disposed in the implant bay;
- an implant disposed in the working fluid; and
- an actuator coupled to the implant bay, the actuator comprising a housing and a plunger having a seal disposed within the implant bay;
- wherein the seal is configured to advance the working fluid and the implant from the implant bay through the delivery lumen.

13. The apparatus of claim 12, wherein the plunger comprises a shaft having a first end and a second end, the seal coupled to the first end.

14. The apparatus of claim 13, further comprising at least one guide fin disposed between the first end and the second end.

15. The apparatus of claim 13, further comprising a plurality of guide fins disposed radially around the shaft between the first end and the second end.

16. The apparatus of claim 13, wherein the shaft is extendable.

17. The apparatus of claim 16, wherein the shaft comprises at least two articulated sections.

18. The apparatus of claim 16, wherein the shaft comprises at least two concertinaed sections.

19. The apparatus of claim 16, wherein the shaft comprises at least two telescoping sections.

20. The apparatus of claim 16, further comprising a fluid coupling proximate to the second end.

21. The apparatus of claim 20, wherein the shaft is configured to be extended by a working fluid pushed through the fluid coupling.

* * * * *